United States Patent [19]

Lapidus

[11] Patent Number: 5,192,333
[45] Date of Patent: Mar. 9, 1993

[54] AQUEOUS PROGRESSIVE HAIR COLORANT HAVING SOLUBLE SULFUR SOURCE AND AMPHOTERIC SURFACTANT

[75] Inventor: Herbert Lapidus, Ridgefield, Conn.

[73] Assignee: Combe Incorporated, White Plains, N.Y.

[21] Appl. No.: 834,387

[22] Filed: Feb. 12, 1992

Related U.S. Application Data

[63] Continuation of Ser. No. 576,787, Sep. 4, 1990, abandoned.

[51] Int. Cl.$^5$ .............................................. A61K 7/13
[52] U.S. Cl. ........................................... 8/405; 8/435; 8/622; 8/626
[58] Field of Search .................. 8/405, 435, 622, 626; 424/70

[56] References Cited

U.S. PATENT DOCUMENTS

| | | | |
|---|---|---|---|
| 3,954,393 | 5/1976 | Lapidus | 8/10.1 |
| 4,104,021 | 8/1978 | Lapidus et al. | 8/10 |
| 4,195,972 | 4/1980 | Lapidus | 8/10.1 |
| 4,306,873 | 12/1981 | Lapidus | 8/405 |
| 4,310,329 | 1/1982 | Holland | 8/404 |
| 4,315,912 | 2/1982 | Kalopissis et al. | 424/70 |
| 4,415,488 | 11/1983 | Blaschke et al. | 252/547 |
| 4,515,775 | 5/1985 | Vanlerberghe et al. | 424/70 |
| 4,583,986 | 4/1986 | Lapidus | 8/405 |
| 4,668,236 | 5/1987 | Grollier et al. | 8/405 |
| 4,668,422 | 5/1987 | Malik et al. | 252/174 |
| 4,692,166 | 9/1987 | Junino et al. | 8/410 |
| 4,740,622 | 4/1988 | Junino et al. | 564/441 |
| 4,749,379 | 6/1988 | Junino et al. | 8/414 |
| 4,834,768 | 5/1989 | Grollier | 8/405 |
| 4,844,712 | 7/1989 | Lapidus | 8/435 |
| 4,865,618 | 9/1989 | Junino et al. | 8/411 |
| 4,911,731 | 3/1990 | Loveless et al. | 8/405 |

FOREIGN PATENT DOCUMENTS

| | | |
|---|---|---|
| 0035364 | 9/1981 | European Pat. Off. . |
| 0070568 | 1/1983 | European Pat. Off. . |
| 3429942 | 3/1986 | Fed. Rep. of Germany . |
| 1498572 | 9/1966 | France . |

OTHER PUBLICATIONS

Cosmetics Science and Technology, vol. 1, 515–524, 1143–1146.
Cosmetics Science and Technology, vol. 2, 325–332.
Handbook of Cosmetic Science (1963) 375–381.

*Primary Examiner*—A. Lionel Clingman
*Assistant Examiner*—William S. Parks
*Attorney, Agent, or Firm*—Fitzpatrick, Cella, Harper & Scinto

[57] ABSTRACT

A clear, aqueous, shelf-stable progressive hair coloring composition includes a salt of a metal, a soluble source of sulfur, an amphoteric surfactant and a pH controller that controls the pH of the composition to be within the range of about 7.5 to about 11.0. Preferred metallic salts are salts of lead or bismuth and the preferred sulfur source is sodium thiosufate.

28 Claims, No Drawings

5,192,333

AQUEOUS PROGRESSIVE HAIR COLORANT HAVING SOLUBLE SULFUR SOURCE AND AMPHOTERIC SURFACTANT

This application is a continuation of application Ser. No. 07/576,787 filed Sep. 4, 1990, now abandoned.

BACKGROUND OF THE INVENTION

1. Field of the Invention

The present invention relates to compositions for dyeing or tinting hair. In particular, the present invention relates to compositions for progressively dyeing hair.

2. Brief Description of the Background Art

The art of dyeing or tinting hair and compositions for the same are generally well known. Although selecting a composition which will dye or tint (hereinafter collectively referred to as "color") hair without unexpected and undesirable results involves a significant amount of experience, the application of modern coloring compositions itself is usually relatively straightforward. In fact, modern colorants are often applied by the individual at home, rather than by a professional.

It will be understood that, for a variety of reasons, many individuals who color their hair do not want that fact to be obvious to others. Therefore, individuals typically select natural colors for their hair, which are often colors close to those that their hair displayed previously. Although such choices minimize the likelihood that others will notice that an individual's hair has been colored, the new color will nevertheless be apparent to close or frequent acquaintances of the individual. This may prove to be embarrassing, for instance, if the individual is self-conscious about having colored hair.

This problem has been previously addressed by utilizing coloring compositions which progressively color hair over a relatively extended period of time (hereinafter referred to as "progressive colorants"). Although multiple successive applications of progressive colorants provide a definite darkening of hair color, progressive colorants are thus characterized by an absence of immediate drastic change in hair color resulting from a single application.

Progressive colorant compositions have utilized metallic dyes, such as lead, silver, nickel, cobalt, copper, bismuth and the like to deposit colored metal salts on the hair. Lead is most commonly employed today in commercial compositions in the form of lead acetate. The lead acetate is present with precipitated sulfur in an aqueous carrier and, when applied to hair, slowly reacts with the sulfur and the sulfur in the hair keratin so as to gradually deposit salts of lead, such as lead sulfide and lead oxide, on the hair cuticle and within the hair shaft.

Although the lead acetate-precipitated sulfur coloring product is now widely used commercially for hair coloring, it has some characteristics that may not be entirely satisfactory to all potential users.

For example, this known commercial product is a cloudy liquid and therefore may give the impression of heaviness or viscousness which on the hair may be perceived to impair the natural appearance of the hair.

Further, if allowed to sit on a shelf for a period of time, this commercial product may show packed precipitated sulfur particles and therefore may require extensive shaking to properly distribute the elemental sulfur for most effective coloring. This characteristic may cause the product to be perceived as "chemical" in nature.

This known commercial product also tends to produce brown hair color. Therefore, potential users whose natural hair color is blonde or light brown may not be entirely happy with the resulting shade.

The known commercial product often requires five to seven days to produce the desired hair color and, in order to achieve that color, shampooing should occur less frequently. Therefore, potential users who ordinarily wish to shampoo more frequently may find this characteristic not to their liking.

Finally, this known commercial product, when in place on the hair, sometimes produces a light sulfur odor that a small percentage of users may notice and find objectionable.

It would, therefore, be advantageous to produce a progressive hair colorant composition with improved characteristics, which could be applied by an individual at home, that a large number of potential users will find very satisfactory.

SUMMARY OF THE INVENTION

Accordingly, it is a general object of the present invention to provide an improvement to the known commercial lead acetate-precipitated sulfur coloring product that is more desirable in that it is a clear, shelf-stable liquid which more quickly produces blonde or light brown hair coloring without odor.

It is a more specific object of the present invention to provide a progressive colorant composition that replaces insoluble precipitated sulfur with a soluble sulfur source and thus is a clear liquid.

It is another object of the present invention to provide a progressive colorant composition that produces hair color more quickly than does the prior art.

It is a further object of the present invention to provide a progressive colorant composition that begins hair coloration more quickly than commercial compositions known in the art.

It is yet another object of the present invention to provide a progressive colorant that produces a natural blonde shade to the hair.

It is a still additional object of the present invention to provide a progressive colorant that permits frequent shampooing.

These objects and others are provided by the present invention of a clear progressive colorant composition comprising a soluble metal salt, a soluble sulfur source, a surfactant, and a pH controller. The surfactant is an amphoteric surfactant and the pH controller may be in the form of an alkanolamine or ammonium hydroxide. This composition is stable and remains clear even during extended time on the shelf.

DETAILED DESCRIPTION OF THE INVENTION

The present invention provides a novel clear progressive hair coloring composition. The active ingredients of the present invention consist of a soluble metal salt, a soluble source of sulfur, a surfactant, and a pH controller that maintains the pH of the composition preferably in the range from about 9.0 to about 10.5.

The metal salt is provided by a progressive-type metallic dye which may be selected from salts of metals that are conventionally utilized in progressive coloranss. As mentioned above, although these metals include lead, silver, nickel, cobalt, copper, bismuth and the like, of this group, lead and bismuth are the preferred choices. Any cosmetically suitable soluble salt of lead or bismuth may be utilized. In the preferred embodiments of the present invention either bismuth subcitrate or lead acetate is used.

The progressive hair coloring composition in accordance with the present invention also comprises a source of sulfur. Inasmuch as the progressive colorant of the present invention need not contain the precipitated elemental sulfur of the prior art, it can be made clear, that is, not cloudy or murky to the casual observer. Rather, the present invention requires a soluble source of sulfur. Although any cosmetically suitable soluble source of sulfur may be utilized, it is desirable to utilize alkaline metal thiosulfates, preferably those selected from sodium, potassium and ammonium thiosulfate. It is especially preferred to utilize sodium thiosulfate in the present invention.

It is believed that the metal salts cannot remain copresent in solution with any soluble (that is, reactive) forms of sulfur since the materials readily form an insoluble metal precipitate. Therefore, when, for example, lead acetate and bismuth subcitrate are utilized, an essential constituent of the present invention is a surfactant capable of forming a complex with cationic metals, in this instance, lead and bismuth. In the preferred embodiments of the present invention, amphoteric surfactants are utilized as they are believed to complex both the soluble lead or bismuth and the soluble sulfur source. These amphoteric surfactants are preferably derived from imidazoline or betaine. If an imidazoline-based surfactant is selected, it is further preferred that it be characterized as having either mono- or dicarboxylic moieties. Preferred examples of the amphoteric surfactant include monosodium lauroamphoglycinate, disodium lauryl aminodipropionate, lauroamphoglycinate, cocoamphopropionate, cocoamphocarboxyglycinate and lauramidopropyl betaine.

It is preferred that the soluble metal salt of the present invention is present in the progressive colorant in the amount of from about 0.03 to about 1.0 weight percent. It will be appreciated that this range will vary depending upon the type of metal (because of its color) which is utilized as the metallic dye and the type of salt which is selected (because of its reactivity). For instance, if lead acetate is selected as the soluble metal salt, it is best that it be utilized in the amount of from about 0.15 to about 0.8 weight percent, with about 0.3 weight percent being preferred. In contrast, if bismuth subcitrate is selected as the soluble metal salt, it is a colloid and is best utilized in the amount of from about 0.05 to about 0.4 weight percent, with the range of from about 0.1 to about 0.15 weight percent being preferred.

Inasmuch as the effectiveness of the present invention depends upon the deposition of an insoluble metallic dye on the hair, it will also be appreciated that the amount of soluble sulfur salt that is present will optimally vary depending upon the type of metal salt which is selected (due to its reactivity) and the amount of metal salt which is utilized (due to equilibrium effects). If, for instance, sodium thiosulfate is selected, it will generally be utilized in the range of from about 0.2 to about 5.0 weight percent. However, since the amount of soluble sulfur which is utilized varies with the kind of soluble metal salt which is selected, it will be understood that more sulfur source will be utilized if lead acetate is the soluble metal salt, for instance, than if bismuth subcitrate is chosen. In particular, if lead acetate is utilized as the soluble metal salt, sodium thiosulfate would be desirably utilized in the range of from about 0.75 to about 4.0 weight percent and preferably at about 2.0 weight percent. In contrast, if, for example, bismuth subcitrate is chosen as the soluble metal salt, sodium thiosulfate would be desirably utilized from about 0.3 to about 4.0 weight percent, and preferably from about 0.5 to about 1.0 weight percent.

As discussed above, the amphoteric surfactant forms a complex with the soluble metal salt and the soluble sulfur source, thereby precluding them from co-reacting while in solution and forming a precipitated metal dye. Most importantly, from the point of view of satisfying the customer, the liquid is clear. Sufficient amounts of amphoteric surfactant must be utilized to complex with substantially all of the soluble salt and soluble sulfur source present in the solution. It is particularly important that a complex be formed with substantially all the metal and sulfur materials which are present since the surfactant-mediated complex is a reversible reaction which is subject to equilibrium constraints, whereas the reaction of soluble metal with soluble sulfur is essentially irreversible.

Generally, from about 0.25 to about 5.0 weight percent of amphoteric surfactant is sufficient to create a stable complex in solution. The preferred range is generally from about 0.50 to about 4.0 weight percent, with about 1.5 weight percent being most preferred for lead acetate and 0.6 weight percent being most preferred for bismuth subcitrate. If, for instance, the surfactant is utilized with lead acetate, to overcome equilibrium effects, it is considered optimal if the surfactant is present at a weight ratio of about 5:1 to lead acetate. If, for example, bismuth subcitrate is chosen as the soluble metal salt, it is considered optimal if the surfactant is present at a weight ratio of about 4:1 to bismuth subcitrate. The above ranges and ratios, of course, vary depending upon the activity of the surfactant which is utilized. The above ranges and ratios are provided for amphoteric surfactants and are based on the concentration of the percent of active surfactant.

Although an aqueous composition comprising the above is initially clear, it has been found that the composition is unstable since within a relatively short time colored precipitates form. This is an undesirable effect when the product sits on a distributor's, retailer's, or customer's shelf. It has been determined that the composition can be made shelf-stable as a clear liquid by controlling the pH of the composition. (For purposes of this application, the maintenance of the clearness of the aqueous composition is characterized as "shelf-stability.") The pH of the solution as formed is generally about 6.0, which has been found to degrade the clearness of the aqueous composition. It has been found that shelf-stability, characterized by the absence of visible precipitates, can be maintained by controlling the pH of the composition in a range of about 7.5 to about 11.0, preferably of about 9 to about 10.5.

An alkanolamine, such as triethanolamine or diethanolamine, and ammonium hydroxide, increase the pH and maintain the stability of the complex solution. Unexpectedly, monoethanolamine functions to maintain the desirable pH in order to maintain the stability of the complex solution while also acting as a dye enhancer to provide color in hair. Monoethanolamine enhances hair color because it allows penetration of the soluble metal salt into the interior of the hair shaft so as to increase the reaction with the natural sulfur of the hair. Monoethanolamine, therefore, is preferred for the production of a progressive hair colorant that yields onset of a deeper color within about two (2) days while also acting as a pH controller to improve shelf-stability.

Other cosmetically acceptable materials may, of course, be included in the progressive colorant. That is, soaps and/or foaming agents may be used to provide a progressive coloring shampoo, colorants may be used to provide desirable tints or hues and perfumes can be used to provide desirable scents to the solution, and other additives may be incorporated to produce further characteristics, such as viscosity or wetting ability and the like. Glycerin, for example, which is included in examples of the present invention set forth below, is a wetting agent. Moreover, water of any type may be used in the composition in accordance with the present invention, while deionized water is preferred. All of these materials are considered to be within the scope of the present invention.

The present invention will now be discussed in terms of specific embodiments. The following Examples are provided solely for additional clarification and are not intended in any manner to limit the present invention.

EXAMPLE 1

| Ingredients | Percent by Total Weight |
| --- | --- |
| Lead acetate | 0.30 |
| Glycerin | 5.00 |
| Deionized water | 87.20 |
| Sodium thiosulfate pentahydrate | 2.00 |
| Lauroamphoglycinate, 30% active | 5.00 |
| Monoethanolamine, 99% | 0.50 |
| | 100.00 |

A progressive colorant having the above formula was prepared by mixing the lead acetate, glycerin and deionized water until the mixture clears. The sodium thiosulfate pentahydrate was then added while mixing. A cloud formed initially and then cleared. After the cloud cleared, the lauroamphoglycinate was blended in. Again, a cloud was formed but then cleared. Thereafter, the monoethanolamine was blended until the mixture was uniform. The composition was then filtered. A stable water white solution having a pH of 10.6 was obtained.

EXAMPLE 2

| Ingredients | Percent by Total Weight |
| --- | --- |
| Lead acetate | 0.50 |
| Glycerin | 5.00 |
| Deionized water | 80.50 |
| Sodium thiosulfate pentahydrate | 3.00 |
| Lauroamphoglycinate, 30% active | 10.00 |
| Monoethanolamine, 99% | 1.00 |
| | 100.00 |

A progressive colorant having the above composition was formed in the same manner as in Example 1 above. The colorant composition also formed a stable water white product having a pH of 10.6.

EXAMPLE 3

| Ingredients | Percent by Total Weight |
| --- | --- |
| Colloidal bismuth subcitrate | 0.125 |
| Glycerin | 2.500 |
| Deionized water | 94.425 |
| Sodium thiosulfate pentahydrate | 0.500 |
| Lauroamphoglycinate, 30% active | 2.00 |
| Monoethanolamine, 99% | 0.250 |
| Dowicil 200 (Quaternium - 15) | 0.200 |
| | 100.000 |

A progressive colorant having the above composition was formed using a process similar to that described in Example 1 by mixing the bismuth subcitrate, glycerin and deionized water until the mixture clears. In individual steps, sodium thiosulfate pentahydrate, lauroamphoglycinate, monoethanolamine and Dowicil are each blended in until the mixture clears. The composition is then filtered. A clear, water white product having a pH of 9 to 10 was obtained. The product remained stable thereafter.

EXAMPLE 4

| Ingredients | Percent by Total Weight |
| --- | --- |
| Colloidal bismuth subcitrate | 0.50 |
| Glycerin | 5.00 |
| Deionized water | 82.50 |
| Sodium thiosulfate pentahydrate | 1.00 |
| Lauroamphoglycinate, 30% active | 10.00 |
| Monoethanolamine, 99% | 1.00 |
| | 100.00 |

A progressive colorant having the above composition was formed using a process similar to that described in Example 1 above. The colorant composition also formed a clear, water-white product having a pH of 10.5. The product remained stable thereafter.

The preferred embodiments specifically described herein provide an improved metallic salt progressive hair colorant that for the first time achieves blonde and light brown hair color. The new composition produces color in about two (2) days and for the first time in the art of known metallic salt dyes permits frequent shampooing without reducing its effectiveness. The clear liquid composition of the invention is stable on the shelf and does not produce a detectable odor in use.

Although several specific embodiments of the invention have been described in detail herein, it is to be understood that the invention is not limited to those embodiments and that various changes and modifications other than those particularly pointed out above can be made by one skilled in the art without departing from the scope or spirit of the invention, as defined in the following claims.

What is claimed is:

1. A clear, aqueous, shelf-stable composition for dyeing human hair, comprising:
    a soluble salt of a metal selected from the group consisting of lead and bismuth;
    a soluble source of sulfur, said salt of a metal and said source of sulfur being in respective amounts sufficient to cause the gradual deposit by said unit of a metal, in the presence of said source of sulfur, of insoluble metallic dye on the cuticle and within the shaft of human hair;

an amphoteric surfactant in an amount sufficient to form a complex both with said salt of a metal and with said source of sulfur; and a pH controller that controls the pH of the composition to be within the range of about 7.5 to about 11.0, thereby producing a clear, shelf-stable composition.

2. The composition of claim 1, wherein said amphoteric surfactant is present in the range of from about 0.25 to about 5.0 weight percent.

3. The composition of claim 1, wherein said metallic salt is present in the range of from about 0.03 to about 1.0 weight percent.

4. The composition of claim 1, wherein said sulfur source is present in the range of from about 0.2 to about 5.0 weight percent.

5. The composition of claim 1, wherein said sulfur source is an alkaline metal thiosulfate.

6. The composition of claim 1, wherein said metallic salt is lead, and is present in the range of from about 0.15 to about 0.8 weight percent.

7. The composition of claim 6, wherein said lead salt is lead acetate.

8. The composition of claim 7, wherein said lead acetate is present at about 0.3 weight percent.

9. The composition of claim 8, wherein said sulfur source is present in the range of from about 0.75 to about 4.0 weight percent.

10. The composition of claim 9, wherein said sulfur source is sodium thiosulfate, and is present at about 2.0 weight percent.

11. The composition of claim 1, wherein said metallic salt is bismuth, and is present in the range of from about 0.05 to about 0.4 weight percent.

12. The composition of claim 11, wherein said bismuth salt is bismuth subcitrate.

13. The composition of claim 12, wherein said bismuth subcitrate is present in the range of from about 0.1 to about 0.15 weight percent.

14. The composition of claim 13, wherein said sulfur source is present in the range of from about 0. to about 4.0 weight percent.

15. The composition of claim 14, wherein said sulfur source is sodium thiosulfate, and is present in the range of from about 0.5 to about 1.0 weight percent.

16. The composition of claim 1, wherein said amphoteric surfactant is a derivative of imidazoline or betaine.

17. The composition of claim 16, wherein said amphoteric surfactant is selected from the group consisting of monosodium lauroamphoglycinate, disodium lauryl aminodipropionate, lauroamphoglycinate, cocoamphopropionate, cocoamphocarboxyglycinate and lauramidopropyl betaine.

18. The composition of claim 17, wherein said amphoteric surfactant is present in the range of from about 0.25 to about 5.0 weight percent.

19. The composition of claim 7, wherein said amphoteric surfactant is selected from the group consisting of monosodium lauroamphoglycinate, disodium lauryl aminodipropionate, lauroamphoglycinate, cocoamphopropionate, cocoamphocarboxyglycinate and lauramidopropyl betaine and is present in the range of from about 0.5 to about 4.0 weight percent.

20. The composition of claim 8, wherein said amphoteric surfactant is selected from the group consisting of monosodium lauroamphoglycinate, disodium lauryl aminodipropionate, lauroamphoglycinate, cocoamphopropionate, cocoamphocarboxyglycinate and lauramidopropyl betaine and is present in the amount of about 1.5 weight percent.

21. The composition of claim 12, wherein said amphoteric surfactant is selected from the group consisting of monosodium lauroamphoglycinate, disodium lauryl aminodipropionate, lauroamphoglycinate, cocoamphopropionate, cocoamphocarboxyglycinate and lauramidopropyl betaine and is present in the range of about 0.25 to about 5.0 weight percent.

22. The composition of claim 13, wherein said amphoteric surfactant is selected from the group consisting of monosodium lauroamphoglycinate, disodium lauryl aminodipropionate, lauroamphoglycinate, cocoamphopropionate, cocoamphocarboxyglycinate and lauramidopropyl betaine and is present in the amount of about 0.6 weight percent.

23. The composition of any one of claims 1 to 23, wherein said pH controller is selected from the group consisting of monoethanolamine, diethanolamine, triethanolamine, and ammonium hydroxide.

24. The composition of claim 23, wherein said pH controller is monoethanolamine present in an amount to produce a pH of the composition of about 9.0 to about 10.5.

25. The composition of claim 7, wherein said amphoteric surfactant is present at a weight ratio of about 5:1 to lead acetate.

26. The composition of claim 12, wherein said amphoteric surfactant is present at a weight ratio of about 4:1 to bismuth subcitrate.

27. A clear, aqueous, shelf-stable composition for dyeing human hair, comprising:

a soluble salt of a metal selected from the group consisting of lead and bismuth;

a soluble source of sulfur, said salt of a metal and said source of sulfur being in respective amounts sufficient to cause the gradual deposit by said salt of a metal, in the presence of said source of sulfur, of insoluble metallic dye on the cuticle and within the shaft of human hair; an amphoteric surfactant present in the range of from about 0.25 to about 5.0 weight percent; and a pH controller that controls the pH of the composition to be within the range of about 7.5 to about 11.0.

28. A clear, aqueous, shelf-stable composition for dyeing human hair, comprising:

a soluble salt of a metal selected from the group consisting of lead and bismuth and being present in the range of from about 0.03 to about 1.0 weight percent;

a soluble source of sulfur being present in the range of from about 0.2 to about 5.0 weight percent;

an amphoteric surfactant being present in the range of from about 0.25 to about 5.0 weight percent; and a pH controller that controls the pH of the composition to be within the range of about 7.5 to about 11.0.

* * * * *

UNITED STATES PATENT AND TRADEMARK OFFICE
CERTIFICATE OF CORRECTION

PATENT NO.   : 5,192,333
DATED        : March 9, 1993
INVENTOR(S)  : HERBERT LAPIDUS It is certified that error appears in the above-identified patent and that said Letters Patent is hereby corrected as shown below:

COLUMN 2

Line 67, "ranss." should read --rants.--.

COLUMN 6

Line 67, "unit" should read --salt--.

COLUMN 7

Line 45, "0." should read --0.3--.

COLUMN 8

Line 47, "an" should read --¶ an--.

Signed and Sealed this

Eleventh Day of January, 1994

Attest:

BRUCE LEHMAN

Attesting Officer     Commissioner of Patents and Trademarks